(12) United States Patent
Bujoli et al.

(10) Patent No.: US 7,521,436 B2
(45) Date of Patent: Apr. 21, 2009

(54) MODIFIED PHOSPHOCALCIC COMPOUND, INJECTABLE COMPOSITION CONTAINING SAME

(75) Inventors: Bruno Bujoli, Sucé sur Erdre (FR); Solen Josse, Cordemais (FR); Jérôme Guicheux, Nantes (FR); Pascal Janvier, Nantes (FR); Jean-Michel Bouler, Nantes (FR); Guy Daculsi, Vigneux de Bretagne (FR)

(73) Assignees: Centre National de la Recherche Scientifique, Paris (FR); Universite de Nantes, Nantes (FR); Institut National de la Sante et de la Recherche Medicale, Paris (FR)

( * ) Notice: Subject to any disclaimer, the term of this patent is extended or adjusted under 35 U.S.C. 154(b) by 290 days.

(21) Appl. No.: 10/506,550

(22) PCT Filed: Feb. 18, 2003

(86) PCT No.: PCT/FR03/00527

§ 371 (c)(1),
(2), (4) Date: Jul. 19, 2005

(87) PCT Pub. No.: WO03/074098

PCT Pub. Date: Sep. 12, 2003

(65) Prior Publication Data

US 2005/0282783 A1    Dec. 22, 2005

(30) Foreign Application Priority Data

Mar. 4, 2002   (FR) .................................. 02 02707

(51) Int. Cl.
*A61K 31/66* (2006.01)
*C07F 9/02* (2006.01)

(52) U.S. Cl. ........................... 514/75; 514/89; 558/156; 548/112; 546/22

(58) Field of Classification Search ................ 514/75, 514/89; 558/156; 548/112; 546/22
See application file for complete search history.

(56) References Cited

U.S. PATENT DOCUMENTS 5,208,234 A * 5/1993 Poss ........................... 514/94

FOREIGN PATENT DOCUMENTS

WO         00/47214 A1    8/2000

OTHER PUBLICATIONS

Bikhman et al., 1981, CAS: 94:1762.*
Kostromina et al., 2001, CAS: 136: 75305.*
Cohen et al., 1998, CAS: 129:49620.*
Zaheer et al., 2001, CAS: 136:163487.*
H. Denissen et al., "Ceramic hydroxyapatite implants for the release of bisphosphonate," *Bone and Mineral*, 1994, pp. 123-134, vol. 25, No. 2, Elsevier Science Ireland Ltd., Shannon, Ireland, XP-001015353.
H. Denissen et al., "Alveolar Bone Response to Submerged Bisphosphonate-Complexed Hydroxyapatite Implants," *Journal of Periodontology*, 2000, pp. 279-286, vol. 71, No. 2, US XP-008010275.
H. Denissen et al., "Net-shaped hydroxyapatite implants for release of agents modulating periodontal-like tissues," *Journal of Periodontal Research*, 1997, pp. 40-46, vol. 32, No. 1, Denmark XP-008010473.

* cited by examiner

*Primary Examiner*—Rei-tsang Shiao
(74) *Attorney, Agent, or Firm*—Buchanan Ingersoll & Rooney PC

(57) ABSTRACT

The invention concerns a phosphocalcic compound modified by a gem-bisphosphonic acid or one of its salts, a method for preparing same, as well as its use for preparing an injectable composition. The modified phosphocalcic compound is obtained by adding a gem-bisphosphonic acid or one of its alkali metal or alkaline earth salts to a suspension of a precursor phosphocalcic compound in ultra-pure water, while stirring the reaction medium at room temperature, then in recovering by centrifuging the formed compound. Said compound is useful for making an injectable composition, for use in the treatment of bone remodeling equilibrium.

17 Claims, 3 Drawing Sheets

MODIFIED PHOSPHOCALCIC COMPOUND, INJECTABLE COMPOSITION CONTAINING SAME

Figure 1:
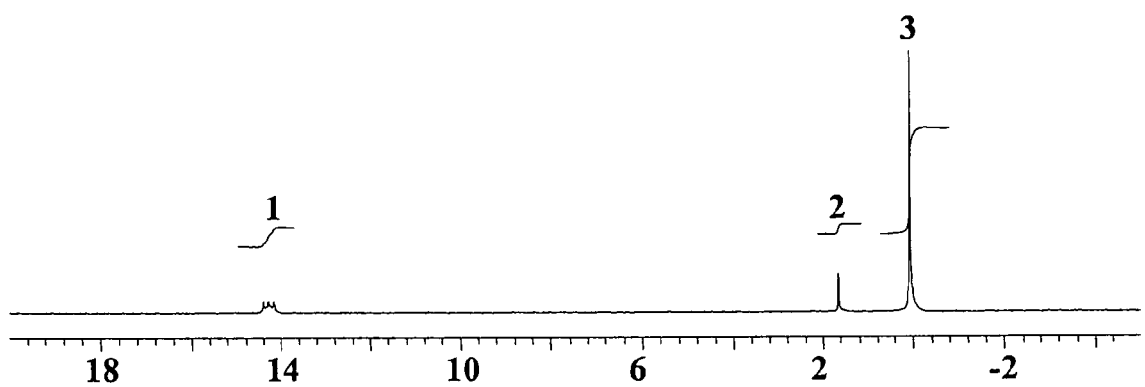

This is application is a 371 of PCT/FR03/00527 filed on Feb. 18, 2003.

The invention relates to a phosphocalcic compound modified with a gem-biphosphonic compound, to a process for preparing it and to its use for producing an injectable composition.

Deregulation of the bone activity of an individual is the cause of many bone pathologies such as osteoporosis, Paget's disease or osteolytic tumors. Taking into account, in particular, the increase in human life expectancy, osteoporosis has become a public health problem and much research has been undertaken to remedy it. Since the bone pathologies under consideration are caused by an imbalance in bone remodeling to the benefit of the activity of the osteoclasts, one of the routes of treatment envisioned consisted in reducing the activity of the osteoclasts, in order to slow down the degradation of the bone material.

Studies performed on various gem-biphosphonic acids have shown their inhibitory power on osteoclast activity (G. A. Rodan et al., Therapeutic Approaches to Bone Diseases, 1 Sep. 2000, Vol. 289, Science, pp. 1508-1514). The use of some of them as medicaments, especially etidronate, clodronate, pamidronate, alendronate, risedronate, tiludronate and ibandronate, has been accepted in various countries. Data have been published for other gem-biphosphonic acid compounds, especially zoledronate, incadronate, olpadronate and neridronate. The gem-biphosphonic acids that are used at the present time for the treatment of bone lesions are used systemically and, as a result, give rise to a few undesirable side effects. They can cause renal disorders when they are administered intravenously, and digestive system-disorders, especially esophagitis or stomach ulcers, when they are administered orally [(Lin J. H., Bone 1996; 18; 75-85) or (Thiébauld D. et al., Osteoporos Int. 1994; 76-73)]. Another drawback of the oral administration lies in the low level of absorption of the active principle onto bone material.

Injectable compositions intended to form bone substitutes are moreover known. FR-2 715 853 describes compositions for biomaterials for resorption/substitution of support tissues, comprising a mineral phase composed of BCP or calcium-titanium-phosphate, and a liquid aqueous phase comprising an aqueous solution of a cellulose-based polymer. These injectable compositions contain no active principle.

Noninjectable bone substitutes, which are in the form of implants, are also known. For example, H. Denissen et al. (J. Periodontal, Vol. 71, No. 2, February 2000, pp. 280-296) describes implants of hydroxyapatite modified by absorption of a particular gem-biphosphonic acid, namely (3-dimethylamino-1-hydroxypropylidene)-1,1-biphosphonic acid, or olpadronate. The in situ release of the acid is said to promote bone reconstruction. However, hydroxyapatite itself has the drawback of being very poorly resorbable.

The aim of the present invention is to provide a composition containing an active principle that inhibits the activity of the osteoclasts and that can be administered without producing the side effects associated with a systemic administration or the use of a solid implant.

Accordingly, the subject of the present invention is a modified phosphocalcic compound, a process for preparing it and its use as active principle in an injectable composition.

The modified phosphocalcic compound according to the present invention may be obtained by adding a gem-bisphosphonic acid or an alkali metal or alkaline-earth metal salt thereof to a suspension of a precursor phosphocalcic compound in ultrapure water, by stirring the reaction medium at room temperature, and then recovering the formed compound by centrifugation. The compound may then be purified by washing with ultrapure water, followed by filtering and drying in air at room temperature. The precursor phosphocalcic compound is chosen from calcium orthophosphates with a solubility in water of greater than $4 \times 10^{-59}$ mol.l$^{-1}$. By way of example, mention may be made of BCPs, which are a mixture of hydroxyapatite and of β-tricalcium phosphate (generally denoted as β-TCP) in variable proportions, CDA, which is a calcium-deficient hydroxyapatite (obtained, for example, by alkaline hydrolysis of a calcium hydrogen orthophosphate), and β-TCP.

In the present text, the term "ultrapure water" means water having a resistivity in the region of 18 MΩ cm.

The stirring at room temperature is preferably maintained for a period of between 1 hour and 72 hours, for example for 48 hours. The nature of the stirring and the particle size of the precursor phosphocalcic compound have an effect on the proportion of gem-biphosphonic compound that may be grafted. It is thus preferable, when a given particle size has been selected for the precursor phosphocalcic compound, to adapt the stirring so as not to modify said particle size.

The acids or salts that may be used as gem-biphosphonic compounds correspond to the formula (OY)(OX)P(O)—CR$^1$R$^2$—P(O)(OX)(OY) in which X or Y represent, independently of each other, H or an alkali metal or alkaline-earth metal cation, R$^1$ represents H, OH or a halogen, and R$^2$ represents:

- a hydrogen or a halogen,
- an alkyl radical,
- an aminoalkyl radical in which the amino group optionally bears an alkyl substituent,
- an alkylamino radical,
- an alkyl radical bearing an aromatic substituent comprising at least one N atom,
- an alkyl radical bearing an aromatic thioether group.

When R$^1$ and/or R$^2$ represent a halogen, Cl is particularly preferred.

When R$^2$ is an alkyl radical, alkyls containing from 1 to 6 carbon atoms are preferred.

When R$^2$ is an aminoalkyl radical, radicals NH$_2$(CH)$_n$— in which n is less than 6 are preferred.

When R$^2$ is an alkylaminoalkyl radical, the preferred radicals are radicals R'R"N(CH$_2$)$_m$— in which R' and R" represent, independently of each other, H or an alkyl radical containing up to 5 carbon atoms, and m is less than 6.

When R$^2$ is an alkylamino radical, the radicals R$^C$NH— in which R$^C$ is a cycloalkyl containing from 3 to 7 carbon atoms are preferred.

When R$^2$ is an alkyl radical bearing an aromatic substituent comprising at least one N atom, alkyls containing up to 3 carbon atoms and bearing one pyridyl or imidazolyl group are preferred.

When R$^2$ is an alkyl radical bearing an aromatic thioether group, alkyls containing up to 3 carbon atoms and bearing a phenylthio group in which the phenyl group optionally bears a halogen substituent are preferred.

Among these gem-bisphosphonic compounds, mention may be made of:
etidronate (R$^1$=OH, R$^2$=CH$_3$),
clodronate (R$^1$=Cl, R$^2$=Cl),
pamidronate (R$^1$=OH, R$^2$=—CH$_2$CH$_2$NH$_2$),
alendronate (R$^1$=OH, R$^2$=—(CH$_2$)$_3$NH$_2$),
risedronate (R$^1$=OH, R$^2$=—CH$_2$-3-pyridine),
tiludronate (R$^1$=H, R$^2$=—CH$_2$—S—C$_6$H$_4$—Cl)

ibandronate ($R^1$=OH, $R^2$=—$CH_2$—$CH_2$—N($CH_3$)pentyl),
zoledronate ($R^1$=OH, $R^2$=—$CH_2$-imidazole)
incadronate ($R^1$=H, $R^2$=—NH-(cycloheptyl)),
olpadronate ($R^1$=OH, $R^2$=$CH_2$—$CH_2$—N($CH_3$)$_2$),
neridronate ($R^1$=OH, $R^2$=—($CH_2$)$_5NH_2$)

The acids in which $R^2$ is an alkyl radical bearing an aromatic substituent comprising at least one N atom, such as zoledronate or risedronate, are particularly preferred.

A modified phosphocalcic compound according to the invention is characterized by the following chemical composition:

$Ca_{(10-a)}(Mg, K, Na)_b(PO_4)_{6-c}(HPO_4, CO_3)_d(OH)_{2-e}(F, Cl, CO_3)_f[(OA)(OE)P(O)—CR^1R^2—P(O)(OA)(OE)]_g$, in which A and E represent H, an alkali metal, an alkaline-earth metal or nothing, and in which $R^1$ and $R^2$ have the meaning given above, and 0<a<9; 0<b<2; 0<c<5; 0<d<2; 0<e<2; 0<f<2; g<0.5. When A or E represents H, the oxygen atom that bears it is not linked to the phosphocalcium matrix or it is simply associated therewith by hydrogen bonding. When A or E is "nothing", the oxygen atom that bears it is coordinated to another element of the composition, for example to a Ca.

The gem-biphosphonic acid content of a modified phosphocalcic compound may be determined by UV-visible spectroscopy according to the method described by Ames, B. N., especially in *Methods in Enzymology*, Colowick, S. P. and Kaplan, N. O. Eds, Academic Press, Orlando, 1966, Vol. 8, pp. 115-118. It may also be determined by liquid $^{31}$P NMR. Characterization of the modified phosphocalcic compound may be performed essentially by solid $^{31}$P MAS NMR, which shows both the presence of the phosphocalcic support and that of the active principle.

Another subject of the invention is a composition that may be used by injection for the treatment of osteoporosis or relapses of lytic tumors by inhibition of osteoclast activity. Said composition is a suspension of the modified phosphocalcic compound defined above in a biocompatible gel or solution having a viscosity that allows the transportation of granules of between 40μm and 500μm in size. By way of example, mention may be made of the hydrogels of biological interest described in Chem. Rev. (2001); 101(7): 1869-1879, especially cellulose-based hydrogels or hydrogels based on sodium hyaluronate.

The choice of the particle diameter is guided by the resorption kinetics, on the one hand, and the injection rheology, on the other hand. Particles less than 40μm in diameter have excessively fast bioresorption kinetics, and particles greater than 500μm in diameter have rheology problems on injection. However, it is understood that a small proportion of particles (up to 10% by volume) may have a diameter of less than 40μm or greater than 500μm. An injectable composition according to the invention preferably contains from 40% to 75% by mass of modified phosphocalcic compound, from 60% to 25% by mass of hydrogel, and optionally various additives. The additives are chosen from compounds capable of introducing various ions of biological interest, for instance: $K^+$, $Na^+$, $Zn^{2+}$, $Mg^{2+}$, $CO_3^{2-}$, $HPO_4^{2-}$, $F^-$ or $Cl^-$.

The composition may be prepared by suspending in a suitable medium the modified phosphocalcic compound prepared in a preliminary step. It may also be prepared by precipitating the modified phosphocalcic compound in situ, from a hydrogel defined as previously and precharged with phosphate ions (or calcium ions, respectively), to which will be added a suitable solution containing calcium ions (or phosphate ions, respectively) and the desired concentration of biphosphonic acid.

The mode of combination between the phosphocalcic matrix and the biphosphonic acid differs according to the phosphocalcic matrix used, and this difference is reflected by a different biological efficacy during in vitro tests on osteoclast cultures.

The composition according to the invention, in injectable form, allows the local treatment of a bone problem on the main at-risk sites identified (neck of the femur and body of the vertebrae), using an active principle known for its systemic use that has various drawbacks recalled previously. In addition, the phosphocalcic phase, which acts as a vector for the active principle, exerts an additional effect in the sense that it allows the gem-biphosphonic acid to be held in place, and it constitutes a source of calcium and of phosphate required for stimulation of the bone remodeling. Hydroxyapatite (HA), described in the prior art as a matrix for an implant impregnated with an active principle, does not form part of the phosphocalcic compounds that may be used in the present invention, since it has relatively poor solubility, it intrinsically has poor resorbability, and the introduction of gem-biphosphonic acid reduces the resorbability potential of the phosphocalcic compounds in general.

EXAMPLES

The present invention is described in greater detail by the examples that follow, which are given for illustrative purposes and to which the invention is not limited.

The following compounds and reagents were used:
ultrapure water: water with a resistivity in the region of 18 MΩ cm
sodium zoledronate: gem-biphosphonic acid sold by the company Novartis
sodium tiludronate: gem-biphosphonic acid sold by the company Sanofi-Synthélabo
NaOH-route CDA: calcium-deficient hydroxyapatite obtained by hydrolysis of dicalcium phosphate dihydrate with aqueous NaOH solution (in the form of granules with a particle size of 40-80 μm)
ammonia-route CDA (calcium-deficient hydroxyapatite obtained by hydrolysis of dicalcium phosphate dihydrate with aqueous ammonia), in the form of granules with a particle size of 40-80 μm
β-TCP, in the form of granules with a particle size of 40-80 μm
BCP (75% β-TCP/25% HA) in the form of granules with a particle size of 40-80 μm
BCP (25% β-TCP/75% HA) in the form of granules with a particle size of 40-80 μm.

Example 1

Preparation of a Modified Phosphocalcic Compound

A suspension of calcium phosphate was prepared by introducing 700 mg of BCP with a particle size of 40-80 μm into 3.5 ml of ultrapure water, and 56 mg (0.14 mmol) of zoledronate were added. The suspension was placed in a tube maintained at room temperature, and was stirred with a rotary stirrer at 15 rpm for 48 hours. The suspension was then centrifuged and the pellet was separated from the supernatant.

The solid phase was then washed several times with ultrapure water, and then filtered off and dried at room temperature.

The process was also performed starting with the following phosphocalcic compounds: NaOH-route CDA, ammonia-route CDA and β-TCP.

Characterization of the Modified Phosphocalcic Compounds

The amount of zoledronate incorporated into each of the phosphocalcic matrices was determined by difference, by assaying the amount of zoledronate present in the supernatant. This assay was performed, on the supernatant solution separated from the pellet after centrifugation, by liquid $^{31}$P NMR from preestablished calibration curves. It may also be performed by UV-visible spectroscopy according to the abovementioned method described by Ames.

The results obtained for each of the precursor phosphocalcic compounds are given in the table below. T (%) indicates the zoledronate content in the final product, expressed as mg of active principle per 100 mg of phosphocalcic compound, and P (%) indicates the percentage of zoledronate bound to the compound relative to the amount introduced into the reaction medium:

| Precursor | T (%) | P (%) |
| --- | --- | --- |
| BCP (75% β-TCP/25% HA) | 1 | 13 |
| BCP (25% β-TCP/75% HA) | 2.7 | 33 |
| NaOH-route CDA | 5.2 | 65 |
| Ammonia-route CDA | 6.4 | 80 |
| β-TCP | 6.4 | 80 |

FIG. 1 represents the liquid $^{31}$P NMR spectrum of the supernatant obtained after centrifugation of the reaction medium corresponding to the CDA precursor (NaOH route). The integration of the signals takes into account the abundance of each species and the chemical shift (characteristic of the species) is given on the x-axis. Peak 1 represents the zoledronate content, peak 2 represents the phosphate released into the medium by the phosphocalcic compound and peak 3 represents the NaH$_2$PO$_4$ reference.

The liquid $^{31}$P NMR spectrum of the compounds obtained from the other precursors (except hydroxyapatite) is similar, and a release of phosphate during reaction is noted in all cases.

Figure 2:
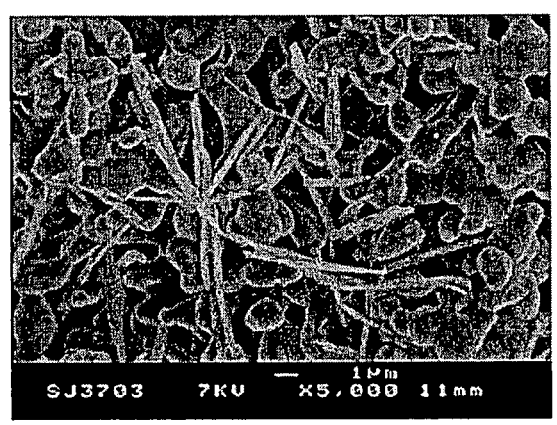

The characterization of the solids obtained shows two different modes of combination of the zoledronate according to the nature of the starting phosphocalcic compound. FIG. 2 shows a photograph by scanning electron microscopy (SEM) performed on the compound obtained from β-TCP. It shows that one form of zoledronate (probably associated with calcium) crystallizes at the surface of the phosphocalcic matrix. The same phenomenon is observed in the case of the BCPs, whether they are rich in β-TCP (75% β-TCP–25% HA) or poor in β-TCP (25% β-TCP–75% HA).

Figure 3:
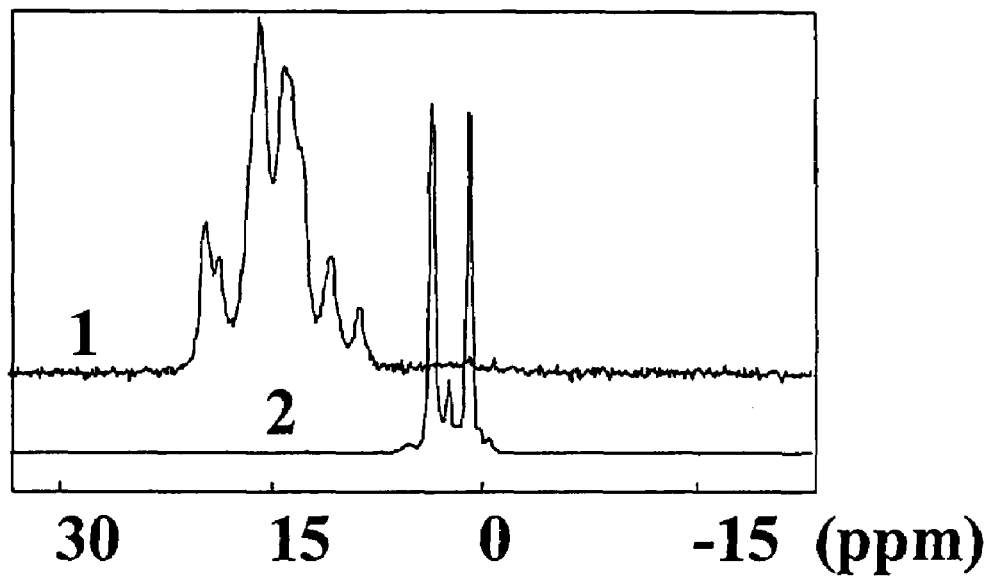

The solid $^{31}$P MAS NMR data are represented in FIG. 3 for the compound obtained from β-TCP. Spectrum 1 acquired in CP (cross-polarization) mode makes it possible to selectively observe the incorporated zoledronate. The fine signals indicate its presence in a crystalline form. Spectrum 2 recorded in proton-decoupling mode makes it possible to selectively observe the unchanged β-TCP support.

Figure 4:
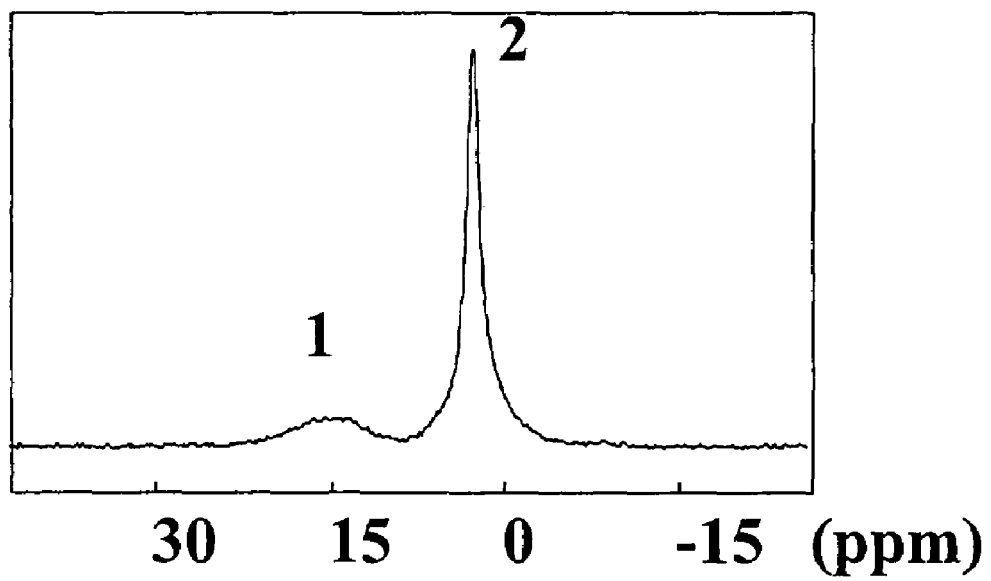

The solid $^{31}$P CP-MAS NMR spectrum is represented in FIG. 4 for the compound derived from CDA (ammonia route). The signal for the zoledronate (peak 1) is very broad. No crystalline phase is detected at the surface of the material, which probably indicates chemosorption of the zoledronate at the surface of the CDA. Peak 2 is characteristic of CDA.

Example 2

Preparation of Phosphocalcic Compounds Modified with Tiludronate and Methylenebiphosphonic Acid A suspension of calcium phosphate was prepared by introducing 700 mg of β-TCP with a particle size of 40-80 μm into 3.5 ml of ultrapure water and 52.5 mg (0.14 mmol) of tiludronate were added. The suspension was placed in a tube maintained at room temperature, and was stirred with a rotary stirrer at 16 rpm for 48 hours. The suspension was then centrifuged and the pellet was separated from the supernatant.

The solid phase was then washed several times with ultrapure water, and then filtered off and dried at room temperature.

Figure 5:
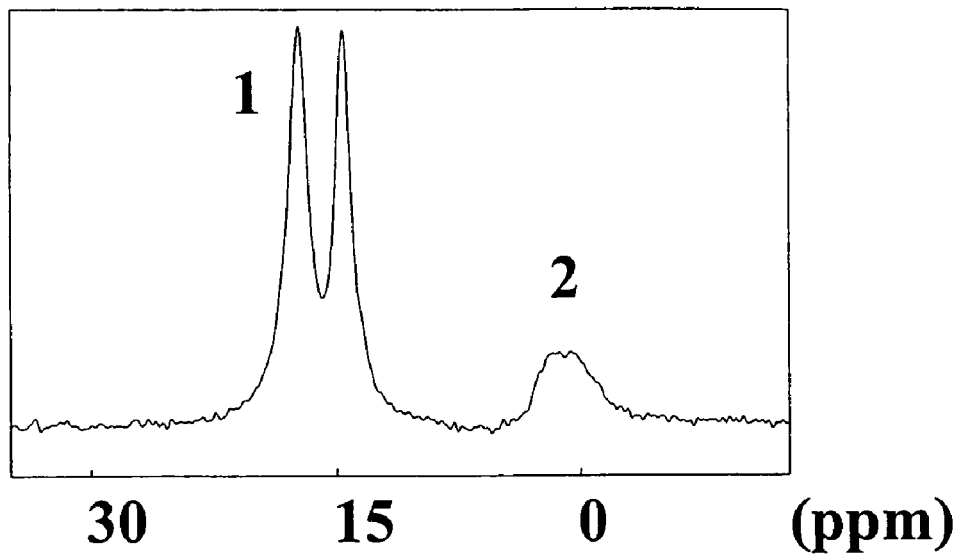

Reactivity similar to that recorded with zoledronate is observed. FIG. 5 shows the $^{31}$P CP-MAS spectrum of the β-TCP treated with tiludronate. The tiludronate may be observed in the form of a crystalline phase (mulitplet 1 consisting of fine signals) deposited on the phosphocalcic phase (which appears weakly (mulitplet 2)) under these conditions in which the spectrum was recorded.

Example 3

Preparation of an Injectable Composition

An injectable composition was prepared from each of the modified compounds obtained in examples 1 and 2, with the exception of the modified compounds obtained from hydroxyapatite, according to the following process.

For each modified compound, granules were prepared, 95% by volume of which granules had an equivalent particle diameter of between 40 and 80 μm, and these granules were introduced into an aqueous solution containing 3% hydroxypropylmethylcellulose comprising 21% by mass of methyl group and 8% by mass of hydroxypropyl group with a degree of polymerization equal to 100, so as to obtain a composition comprising 49% by mass of granules.

Each of the compositions thus prepared was introduced into a glass bottle and sterilized in an autoclave at 121° C. for 20 minutes.

Example 4

In Vitro Tests of Modified Calcium Phosphates

Total bone cells, isolated from long bones of newborn rabbits, were used to evaluate the efficacy of the combination of the modified phosphocalcic compound. The performance qualities of the modified BCP and of the modified ammonia-route CDA obtained in example 1 were measured and compared with those of the respective phosphocalcic precursor not treated with the gem-biphosphonic acid.

For each test, two pellets of sperm whale dentine (reference compound for measuring the resorption) and one pellet of untreated phosphocalcic compound were placed in a first culture well, and two pellets of dentine and one pellet of surface-treated phosphocalcic compound were placed in a second culture well.

The resorption activity of the osteoclasts under these culture conditions was evaluated (after five days) by three different parameters:

1—the total number of spaces formed at the surface of the sperm whale dentine
2—the average surface area of the spaces
3—the surface area of resorbed dentine.

It is seen that:
In the presence of BCP pellets modified with 1% by weight of zoledronate, the residual resorption activity of the bone cells of the model was undetectable. This phenomenon is thought to be associated with a substantial release of zoledronate which had a cytotoxic effect. Specifically, if modified β-TCP or BCP is placed in water, a significant percentage of the zoledronate loaded rapidly returns into solution. For example, 60 mg of modified β-TCP suspended in 1 ml of water for 8 hours leads to the release of about 25% of the loaded zoledronate, i.e. a molar concentration of $10^{-2}$ M.

In the presence of CDA pellets modified with 6.4% by weight of zoledronate, the resorption activity of the cells was reduced by about 80% relative to the zoledronate-free control. As in the case of the modified β-TCP, if 60 mg of modified CDA are suspended in 1 ml of water for 8 hours, no trace of zoledronate is detected (UV-visible method). This implies that the zoledronate is potentially present only at concentrations of less than $10^{-4}$ M (detection limit under our analysis conditions).

These results show that the performance qualities of the material result not only from the amount of zoledronate bound to the phosphocalcic matrix, but also from the rate of release of the zoledronate, and they confirm a remote effect of the modified phosphocalcic matrix.

Example 5

Several samples of CDA (200 mg) modified by adding zoledronate in accordance with the process of example 1 and several samples of unmodified CDA were incubated in 5 ml of culture medium at 37° C. After incubation for 96 hours, the various supernatants were collected and used pure, diluted 10-fold, 100-fold and 1000-fold in a rabbit osteoclast model.

Figure 6:
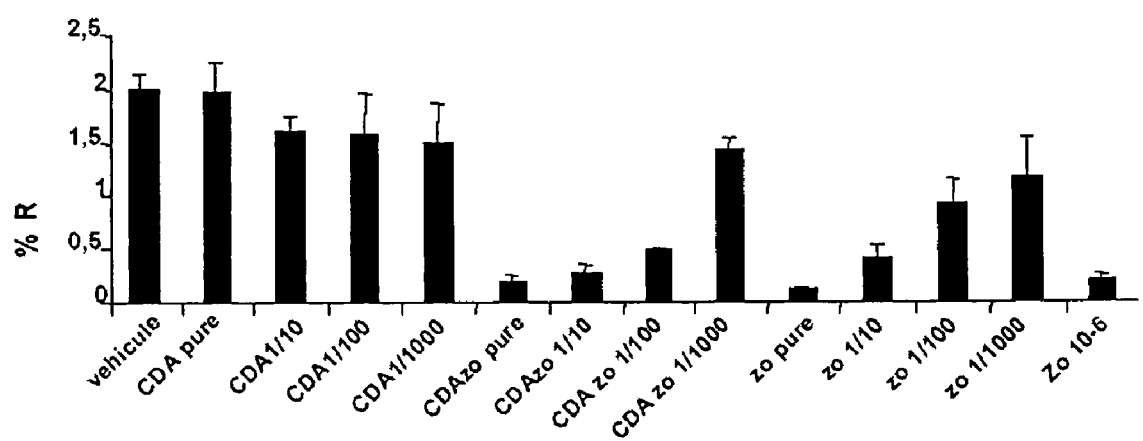

The results are represented in FIG. 6, in which the percentage of resorption R is indicated on the y-axis, the conditions being indicated on the x-axis. Among the conditions:
  "vehicle" means the culture medium alone
  "pure CDA" means the supernatant derived from the incubation of pure CDA in the culture medium; "CDA 1/10", "CDA 1/100" and "CDA 1/1000" mean, respectively, the solution referred to above and diluted to 1/10, 1/100 and 1/1000
  "pure zo" means a $10^{-6}$ M solution of zoledronate in the culture medium, "zo 1/10", "zo 1/100" and "zo 1/1000" mean, respectively, the solution referred to above and diluted to 1/10, 1/100 and 1/1000
  "pure CDAzo" means the supernatant derived from the incubation of zoledronate-containing CDA in the culture medium, and "CDAzo 1/10", "CDAzo 1/100" and "CDAzo 1/1000" mean, respectively, the solution referred to above and diluted to 1/10, 1/100 and 1/1000.

These results show that:
  the zoledronate released by the phosphocalcic phase (CDAzo) retains its inhibitory activity on osteoclast resorption with a pronounced dose effect,
  CDA alone does not appear to influence the osteoclast resorption, irrespective of the dilution of the supernatant,
  zoledronate in solution (zo) retains its biological activity and inhibits resorption according to a dose/effect relationship.

The comparison of the profiles of inhibition of osteoclast resorption induced by the CDA/zo combination and by zoledronate alone ($10^{-6}$ M solution used pure, diluted 10-fold, 100-fold and 1000-fold) makes it possible to suggest that the material releases an amount of zoledronate corresponding to a concentration of about $10^{-6}$ M.

The invention claimed is:

1. A phosphocalcic compound, having the following chemical composition:

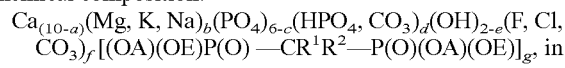

in which $0<a<9$; $0<b<2$; $0<c<5$; $0<d<2$; $0<e<2$; $0<f<2$; $g<0.5$, A and E represent H, an alkali metal, an alkaline-earth metal or nothing, $R^1$ represents H, OH or a halogen and $R^2$ represents an element chosen from a hydrogen, a halogen, an alkyl radical, an aminoalkyl radical in which the amino group optionally bears an alkyl substituent, an alkylamino radical, an alkyl radical bearing an aromatic substituent having at least one N atom wherein the aromatic substituent is not imidazolyl or pyridyl, and an alkyl radical bearing an aromatic thioether group.

2. The compound as claimed in claim 1, wherein $R^1$ and/or $R^2$ represent Cl.

3. The compound as claimed in claim 1, wherein $R^2$ is a radical containing from 1 to 6 carbon atoms.

4. The compound as claimed in claim 1, wherein $R^2$ is an aminoalkyl radical $NH_2(CH)_n$— in which n is less than 6.

5. The compound as claimed in claim 1, wherein $R^2$ is an alkylaminoalkyl radical $R'R''N(CH_2)_m$— in which R' and R'' represent, independently of each other, H or an alkyl radical containing up to 5 carbon atoms, and m is less than 6.

6. The compound as claimed in claim 1, wherein $R^2$ is an alkylamino radical $R^c NH$— in which $R^c$ is a cycloalkyl containing from 3 to 7 carbon atoms.

7. The compound as claimed in claim 1, wherein $R^2$ is an alkyl radical containing up to 3 carbon atoms and bearing a phenylthio group in which the phenyl group optionally bears a halogen substituent.

8. The compound as claimed in claim 1, wherein $R^1$ is OH, A and E represent H.

9. A process for preparing a modified phosphocalcic compound as claimed in claim 1, comprising adding a gem-biphosphonic acid or an alkali metal or alkaline-earth metal salt thereof to a suspension of a precursor phosphocalcic compound in ultrapure water, stirring the reaction medium at room temperature and then recovering the formed compound therefrom by centrifugation.

10. The process as claimed in claim 9, wherein the compound formed is purified by washing with ultrapure water, followed by filtering and drying in air at room temperature.

11. The process as claimed in claim 9, wherein the precursor phosphocalcic compound is chosen from calcium orthophosphates with a solubility in water of greater than $4\times10^{-59}$ $mol.l^{-1}$.

12. The process as claimed in claim 11, wherein the phosphocalcic compound is chosen from BCP, CDA, which is a calcium-deficient hydroxyapatite, and β-TCP.

13. The process as claimed in claim 9, wherein the stirring at room temperature is maintained for a period of between 1 hour and 72 hours.

14. The process as claimed in claim 9, wherein the acids or salts used as gem-biphosphonic compounds correspond to the formula $(OY)(OX)P(O)$—$CR^1R^2$—$P(O)(OX)(OY)$ in which X or Y represent, independently of each other, H or an alkali metal or alkaline-earth metal cation, $R^1$ represents H, OH or a halogen, and $R^2$ represents:
  a hydrogen or a halogen,
  an alkyl radical,
  an aminoalkyl radical in which the amino group optionally bears an alkyl substituent,
  an alkylamino radical,
  an alkyl radical bearing an aromatic substituent having at least one N atom, or
  an alkyl radical bearing an aromatic thioether group.

15. A composition, comprising a suspension of the modified phosphocalcic compound as claimed in claim 1, in a biocompatible gel or solution having a viscosity that allows the transportation of granules of between 40 μm and 500 μm in size.

16. The composition as claimed in claim 15, wherein the biocompatible gel is a hydrogel.

17. The composition as claimed in claim 16, wherein the gel is cellulose-based hydrogen or a hydrogel based on sodium hyaluronate.

* * * * *